(12) United States Patent
Bell

(10) Patent No.: US 6,183,440 B1
(45) Date of Patent: Feb. 6, 2001

(54) HYPODERMIC SYRINGE HAVING A SELECTIVELY RETRACTABLE NEEDLE

(75) Inventor: Jon S. Bell, Waldwick, NJ (US)

(73) Assignee: Becton, Dickinson and Company, Franklin Lakes, NJ (US)

( * ) Notice: Under 35 U.S.C. 154(b), the term of this patent shall be extended for 0 days.

(21) Appl. No.: 09/578,601

(22) Filed: May 25, 2000

(51) Int. Cl.[7] .................................................. A61M 5/50
(52) U.S. Cl. .......................................... 604/110; 604/198
(58) Field of Search ................................... 604/110, 111, 604/136, 138, 162, 157, 192, 195, 197, 198, 230, 236, 263

(56) References Cited

U.S. PATENT DOCUMENTS

| | | |
|---|---|---|
| 4,747,831 | 5/1988 | Kulli . |
| 4,838,863 | 6/1989 | Allard et al. . |
| 4,838,869 | 6/1989 | Allard . |
| 4,900,307 | 2/1990 | Kulli . |
| 4,927,414 | 5/1990 | Kulli . |
| 5,053,010 * | 10/1991 | McGary et al. ...................... 604/110 |
| 5,084,018 * | 1/1992 | Tsao ...................... 604/110 |
| 5,188,599 * | 2/1993 | Botich et al. ...................... 604/110 |

* cited by examiner

*Primary Examiner*—Anhtuan T. Nguyen
(74) *Attorney, Agent, or Firm*—Arthur D. Dawson

(57) ABSTRACT

A syringe includes an elongate barrel having an open proximal end and a distal end that includes a fitting. It also has a plunger having a proximal end and a distal end, sized for slidable movement within the barrel thereby defining a chamber within the barrel. The plunger also has an elongate cavity therewithin that has a closed proximal end and an open distal end. The open end of the plunger is closed by a selectively releasable closure. The syringe has a hub that attaches to the barrel with a fitting conjugate to the fitting. The hub includes an elongate needle having a proximal end, a distal end and a fluid path therethrough. The needle is positioned in the passageway for slidable movement between a first position wherein the fluid path of the needle is in fluid communication with the chamber and a second position. The needle has a mount at its proximal end forming a seal with the chamber when the needle is in the first position. The syringe has a spring disposed about the mount biased to urge slidable movement of the needle from the first position. The syringe includes a latch disposed in the hub to engage the mount and retain the mount in the first position. The latch is releasable so that the spring urges the needle to move from the first into the second position within the cavity in the plunger, once the latch is released.

20 Claims, 16 Drawing Sheets

HYPODERMIC SYRINGE HAVING A SELECTIVELY RETRACTABLE NEEDLE

FIELD OF THE INVENTION

The present invention is generally related to medical devices and more particularly to hypodermic syringes having a needle that is selectively retractable into the syringe by the practitioner.

BACKGROUND

In the medical device field, many devices are designed to provide a practitioner with access through the skin of a patient. In order to provide this access, the devices often incorporate some sort of "sharp". Exemplary of these devices are scalpels, hypodermic syringe needles, catheter placement needles and the like. Both catheter placement needles and hypodermic syringe needles are necessarily elongate, slender and very sharp. Most of these needles are intended for only a single use, and once used for their intended purpose are considered hazardous to anyone who may have reason to encounter them, including the practitioner who is using the device, those assisting the practitioner and any support staff who may be involved in the ultimate disposal of the devices. The hazards related to used "sharps" medical devices are well reported and need not be further dwelt upon here.

There are many products, both patented and unpatented, that are available to practitioners and support staff to assist in the handling and disposal of such sharps. Additionally, there continues to be a need for controlling the disposal of used hypodermic syringes and needles to prevent their salvage and reuse by users of intravenous illicit drugs. Initial efforts to protect practitioners and support staff from used needles included devices to cut off needles, various kinds of receptacles for receiving and disposing of sharps. More recently, specialized shielding devices and retractable needles have been disclosed. Early examples of the efforts in retractable needles as applied to syringes are provided by Allard, et al. in U.S. Pat. Nos. 4,838,863 and 4,838,869.

U.S. Pat. No. 4,838,863 discloses a hypodermic syringe with an cylindrical outer body adapted to accept a smaller fluid storage within the inner walls thereof that has a removable cap on one end of the cylinder for providing access to insert and remove vial. The disclosed syringe further includes a spring loaded double headed needle that is held in place by a retainer until the storage vial has been punctured by the end of the needle, the vial filled and removed. The needle is then retracted into the space vacated by the vial.

U.S. Pat. No. 4,838,869 discloses a retractable hypodermic needle configured for one-time use wherein the needle is spring loaded and automatically irretrievably retracted into the hypodermic syringe when the syringe plunger is fully depressed, whereby protrusions on the end of the plunger engage tabs holding the spring loaded needle to release the needle for retraction. Since hypodermic syringes are used for many different procedures, a syringe that has a needle that automatically retracts once the plunger is depressed and withdrawn, a hypodermic syringe based on the disclosure of this patent may not be suitable for many procedures.

A series of patents to Kulli, beginning with U.S. Pat. No. 4,747,831 that discloses a cannula insertion set with a safety retracting needle, provide practitioners with a needle that is selectively retractable. The '831 patent discloses a cannula insertion needle that projects forward from a hollow handle. The needle has a selectively releasable latch that retains the needle in the projecting forward position against a biasing spring. The hollow handle includes a chamber that is sized to allow the needle to be completely withdrawn into the chamber by the spring when the practitioner releases the latch. In a subsequent disclosure, U.S. Pat. No. 4,927,414, Kulli discloses a syringe having a barrel with a hollow elongate chamber, surrounded by a plunger for drawing and dispensing liquids. The disclosed syringe has a needle projecting outwardly that is selectively releasable into the hollow chamber when the practitioner has completed the desired procedure. The syringe disclosed in this procedure is complex, having many parts, and a commercial product based on this disclosure has never been produced. Another disclosure by Kulli, U.S. Pat. No. 4,900,307 discloses syringe needle that includes a hub with a chamber similar to that disclosed in the 4,747,831 patent for the insertion. A syringe manufactured according to the disclosure in the '307 patent, while satisfactory for some procedures, would retain a substantial volume of undeliverable medicament, "dead space", and no successful commercial product based on this disclosure is available. The Kulli disclosures contain additional references and descriptions of other retractable needle devices that provide additional background related to the area of protected needle devices.

As illustrated by the above references, there is recognition in the medical device field of the desirability of a hypodermic needle that provides the practitioner and support staff with protection from inadvertent exposure to a used sharp point of a needle. While the referenced disclosures address some of the needs, none of them have resulted in commercially successful hypodermic syringes. If a hypodermic syringe were available that had substantially no more dead space than conventional commercial syringes, had a needle that was selectively releasable by the practitioner and additionally, was not as complex, thus facilitating its manufacture, the art of hypodermic syringes would be advanced. A further benefit would be realized if the syringe was able to accept several different sized needles. Such a hypodermic syringe and needle is disclosed hereinbelow.

SUMMARY OF THE INVENTION

A hypodermic syringe assembly of the invention that is useful for drawing, containing and delivering liquids includes a syringe with an elongate barrel defining an axis, an inside surface, an open bore therethrough having an open proximal end and a distal end that includes a fitting. The syringe also has an elongate plunger having a proximal end and a distal end, the plunger is disposed within the barrel and sized for slidable movement within the open bore of the barrel thereby defining a chamber proximal to the distal end of the barrel within the barrel. The chamber allows for drawing, containing and delivering liquids, with the distal end of the plunger forming a substantially liquid tight seal with the inside surface of the barrel. The plunger also has an elongate cavity therewithin that has a closed proximal end and an open distal end. The open distal end of the plunger is closed by a selectively releasable closure. Additionally, the fitting at the distal end of the barrel has a passageway therethrough into the chamber of the barrel. The syringe assembly of the invention has a hub that attaches to the barrel with a fitting conjugate to the fitting at the distal end of the barrel, the hub having a passageway therethrough communicative to the chamber in the barrel when the hub is attached to the barrel. The hub further includes an elongate needle having a proximal end, a distal end and a fluid path therethrough. The needle is positioned through in the passageway for slidable movement between a first position wherein the fluid path of the needle is in fluid communication with the chamber in the barrel with the distal end of the needle projecting outwardly from the hub and a second position. The needle has a mount at its proximal end with the mount proximal end having a seal portion for forming a seal with the chamber at the distal end of the barrel when the needle is in the first position so that a movement of the plunger within the barrel can draw into and expel a liquid from the chamber through the fluid path of the needle. The syringe assembly of the invention also has a spring disposed about the mount being biased to urge slidable movement of the needle from the first position to the second position. The syringe of the invention further includes a selectively releasable latch disposed in the hub to engage the mount and retain the mount and the needle in the first position. The latch is releasable by a practitioner so that the spring urges the mount and the needle to move from the first position into the second position, the second position being substantially within the cavity in the plunger, thereby substantially protecting the medical practitioner from inadvertent contact with the needle once the latch is released. The movement of the mount and the needle into the cavity in the plunger renders the syringe and needle substantially non-reusable.

The syringe assembly of the invention provides practitioners using hypodermic syringes with a retractable needle syringe that substantially "transparently", i.e., without substantially altering current procedure, allows the practitioner to continue routine syringe usage practices. The assembly of the invention is selectively activatable and is simple to use. In one embodiment, the syringe of the invention is capable of being used with needles of more than one size. When used as a delivery device, the syringe of the invention has substantially less dead space than conventional syringes. Additionally, since the syringe of the invention has fewer parts and a simpler design than many of the current devices, the syringe of the invention is simpler and more efficient to manufacture, thus increasing the likelihood of its commercialization. The syringe assembly of the invention provides the users of hypodermic syringes and their support staff with additional protection from inadvertent exposure to used hypodermic needles with the well-known concomitant hazards of such exposure as well as substantially preventing the salvage and unauthorized reuse of such syringes.

DETAILED DESCRIPTION

Figure 1:
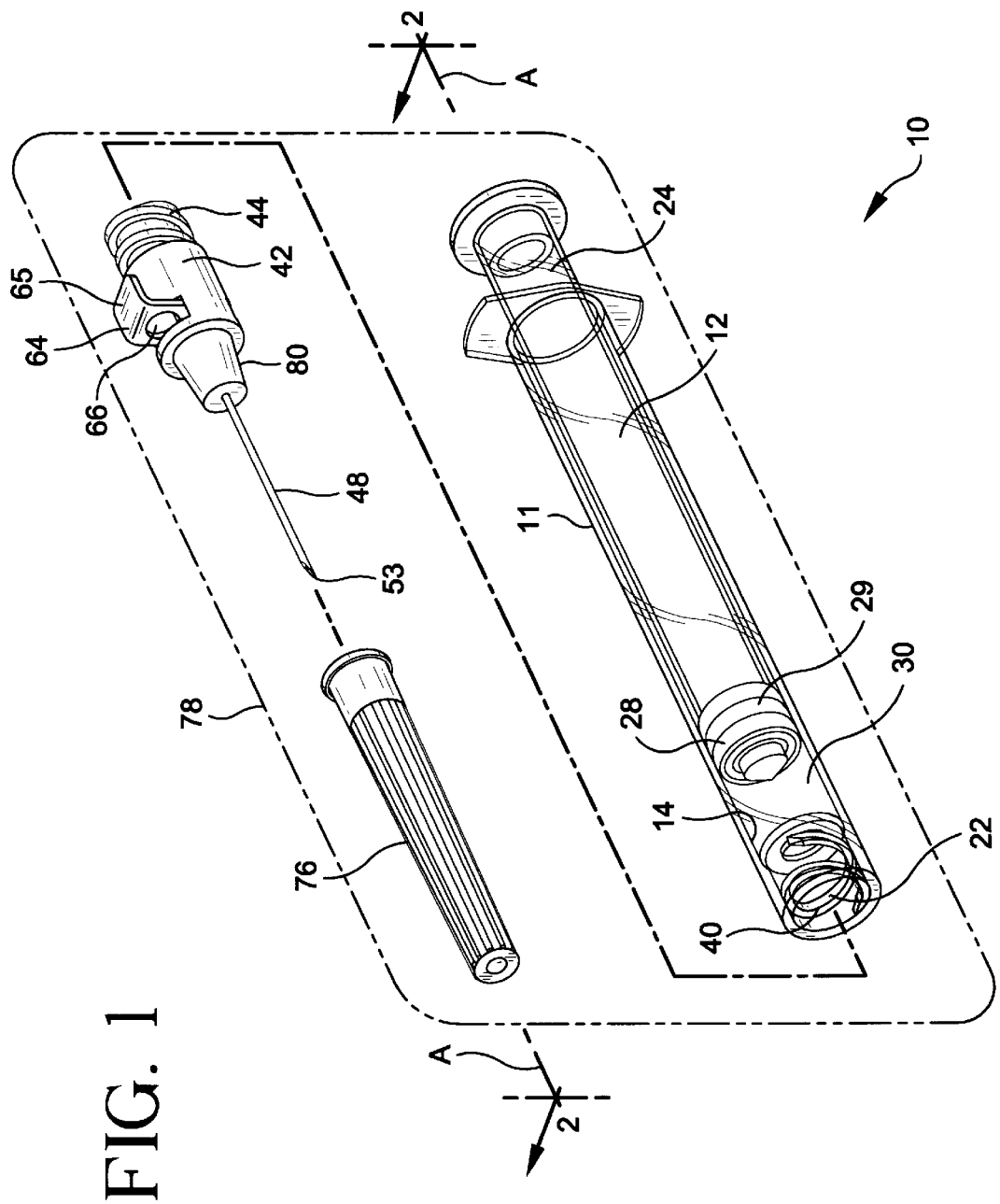
FIG. 1 is a partially exploded perspective view of the syringe and needle of the invention.

While this invention is satisfied by embodiments in many different forms, there are shown in the drawings and herein described in detail, embodiments of the invention with the understanding that the present disclosure to be considered as exemplary of the principles of the present invention and is not intended to limit the scope of the invention to the embodiments illustrated. The scope of the invention is measured by the appended claims and the equivalents. In this disclosure, a convention is followed wherein the distal end of the device is the end closest to a patient and the proximal end of the device is the end away from the patient and closest to a practitioner.

Referring to FIGS. 1–12, a hypodermic syringe assembly 10 of the invention that is useful for drawing, containing and delivering liquids includes a syringe 11 with an elongate barrel 12 defining an axis A, an inside surface 14, an open bore 16 therethrough having an open proximal end 18 and a distal end 20 that includes a fitting 22. Syringe 11 also has an elongate plunger 24 having a proximal end 26 and a distal end 28, plunger 24 is disposed within and sized for slidable movement within open bore 16 of barrel 12 thereby defining a chamber 30 proximal to distal end 20 of the barrel within barrel 12. Chamber 30 allows for drawing, containing and delivering liquids, with distal end 28 of plunger 24 forming a substantially liquid tight seal with inside surface 14 of barrel 12. Plunger 24 also has an elongate cavity 32 therewithin, best seen in FIG. 2, that has a closed proximal end 34 and an open distal end 36. Open distal end 36 of plunger 24 is closed by a selectively releasable closure 38, such as a plug illustrated in FIGS. 5 and 5a.

Additionally, fitting 22 at distal end 20 of barrel 12 has a passageway 40 therethrough into chamber 30 of the barrel 12. Syringe assembly 10 of the invention has a hub 42 that attaches to 12 barrel with a fitting 44 conjugate to fitting 22 at distal end 20 of the barrel 12, hub 42 having a passageway 46 therethrough communicative to chamber 30 in barrel 12 when hub 42 is attached to barrel 12. Hub 42 further includes an elongate needle 48 having a proximal end 50, a distal end 52 and a fluid path 54 therethrough. Needle 48 is positioned in passageway 46 for slidable movement between a first position, best seen in FIG. 3, wherein fluid path 54 of needle 48 is in fluid communication with chamber 30 in the barrel and distal end 52 of the needle projecting outwardly from hub 42 and a second position, best seen in FIGS. 6 and 7. Needle 48 has a mount 56 at proximal end 50 with a mount proximal end 58 of the mount having a seal portion 60 for forming a seal with chamber 30 at the distal end of the barrel when needle 48 is in the first position so that a movement of plunger 24 within the barrel can draw into and expel a liquid from chamber 30 through fluid path 54 of needle 48.

Figure 8:
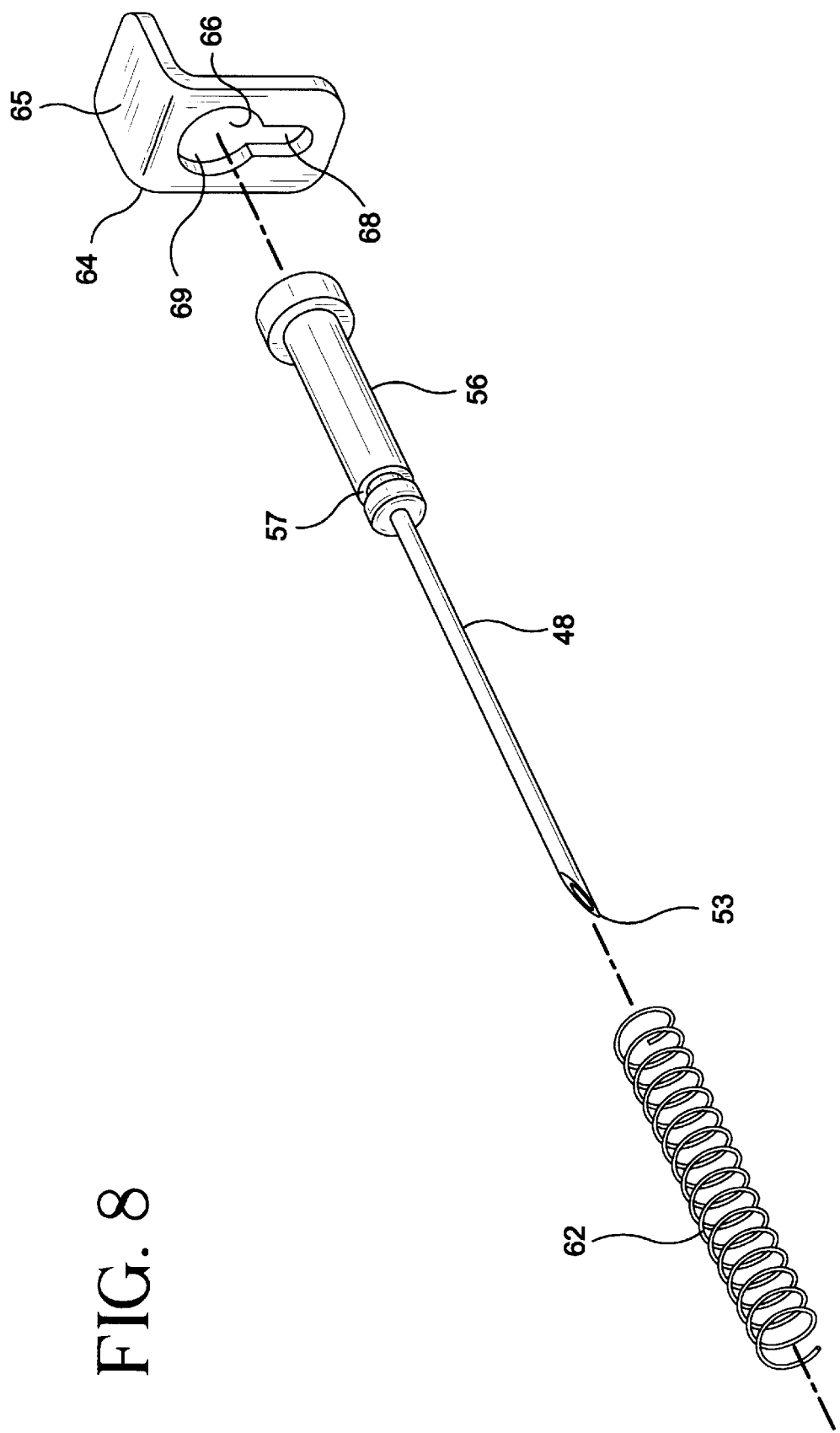
FIG. 8 is an exploded perspective view of the spring, needle, mount and latch portions of the syringe of the invention.
Figure 9:
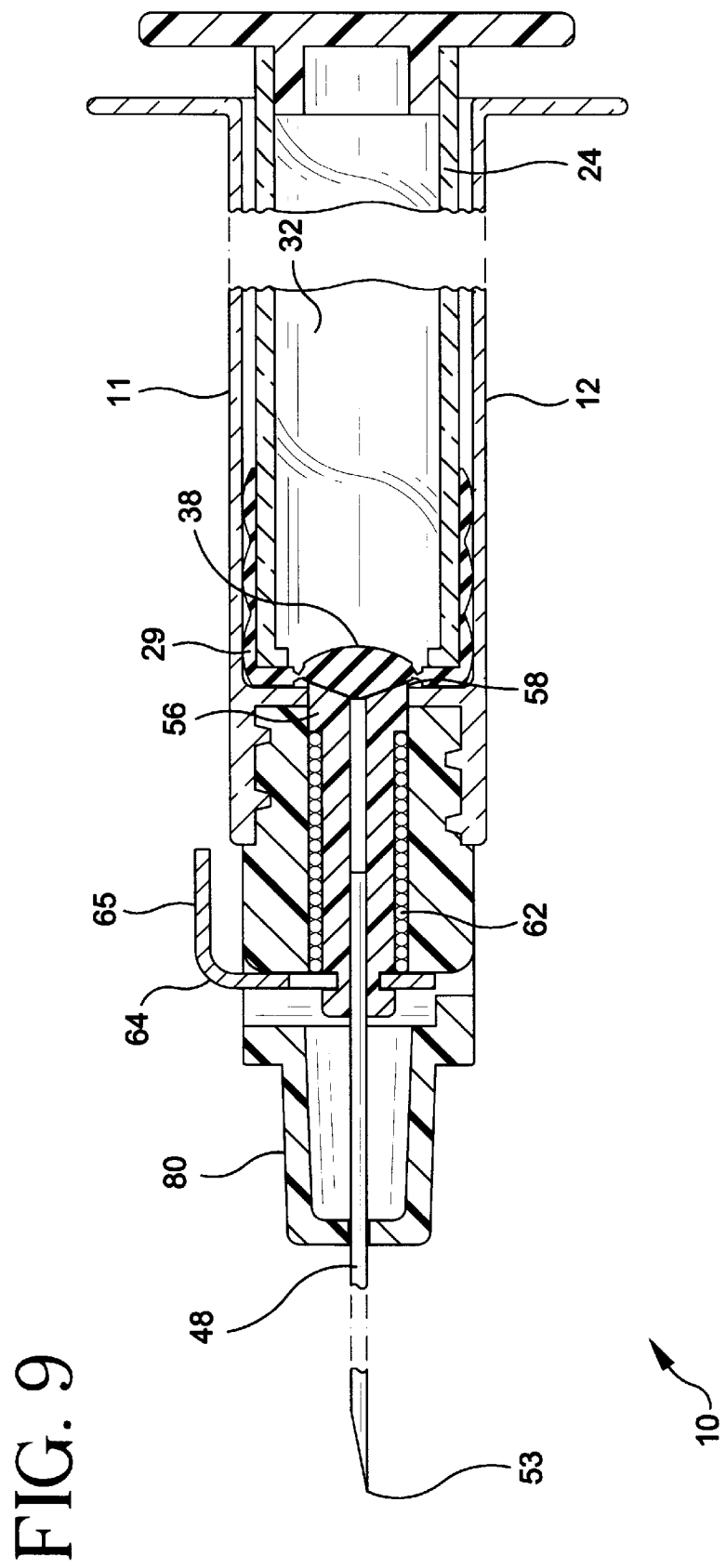
FIG. 9 is a schematic cross-sectional view of an embodiment of the invention of FIG. 1, analogous to the view of FIG. 4, with the plunger depressed to expel the contents of the syringe.
Figure 10:
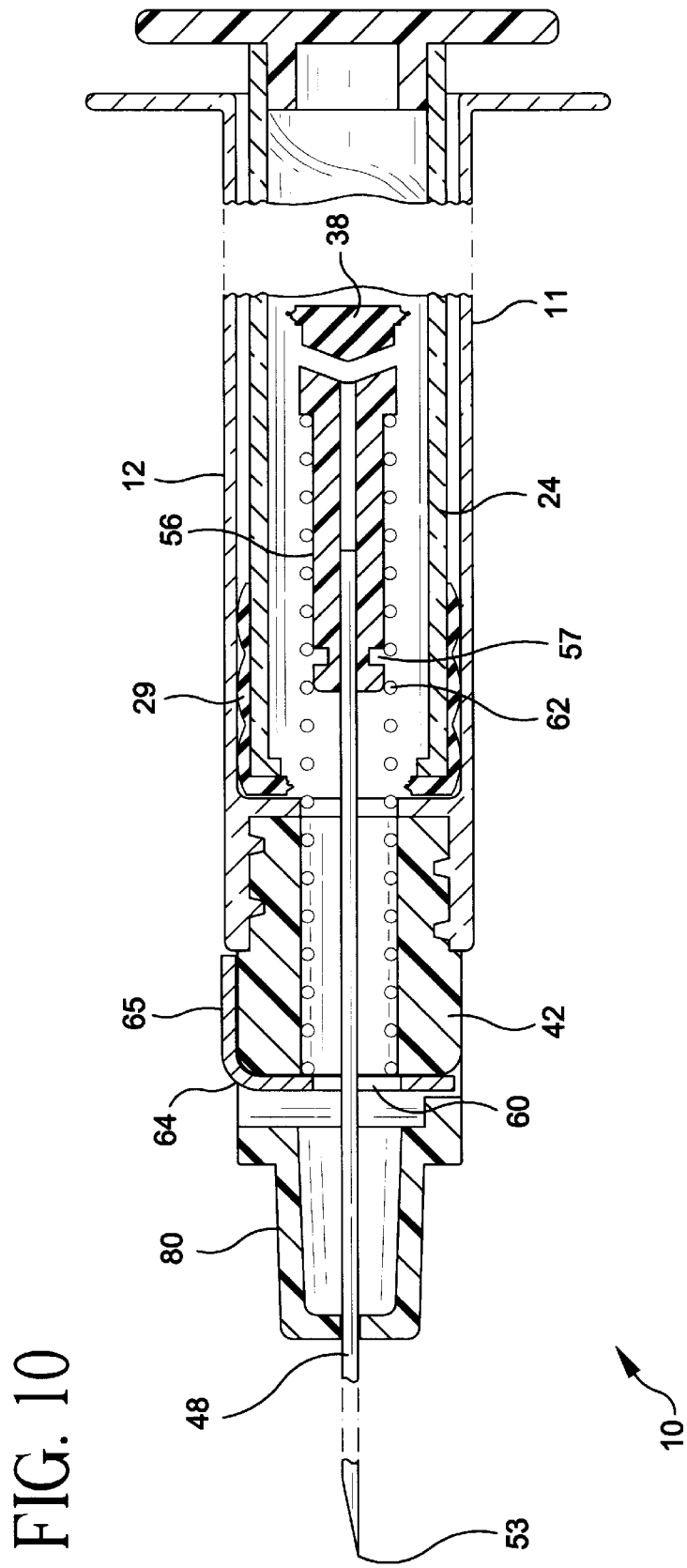
FIG. 10 is a schematic cross-sectional view of the embodiment of FIG. 9, with the latch in the release position and with the needle and the mount partially withdrawn into the cavity in the plunger.
Figure 11:
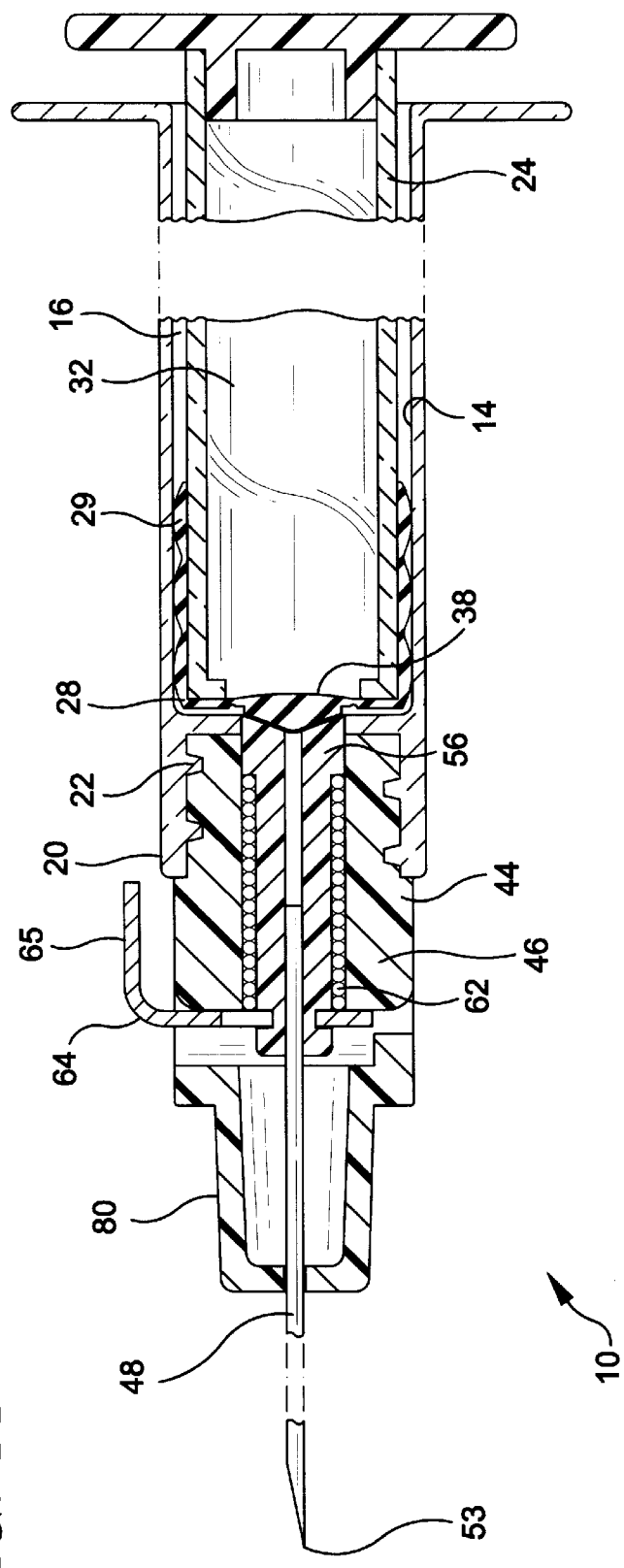
FIG. 11 is a schematic cross-sectional view of another embodiment of the invention of FIG. 1, analogous to the view of FIG. 4, with the plunger depressed beyond the amount require to substantially expel the contents of the syringe.
Figure 12:
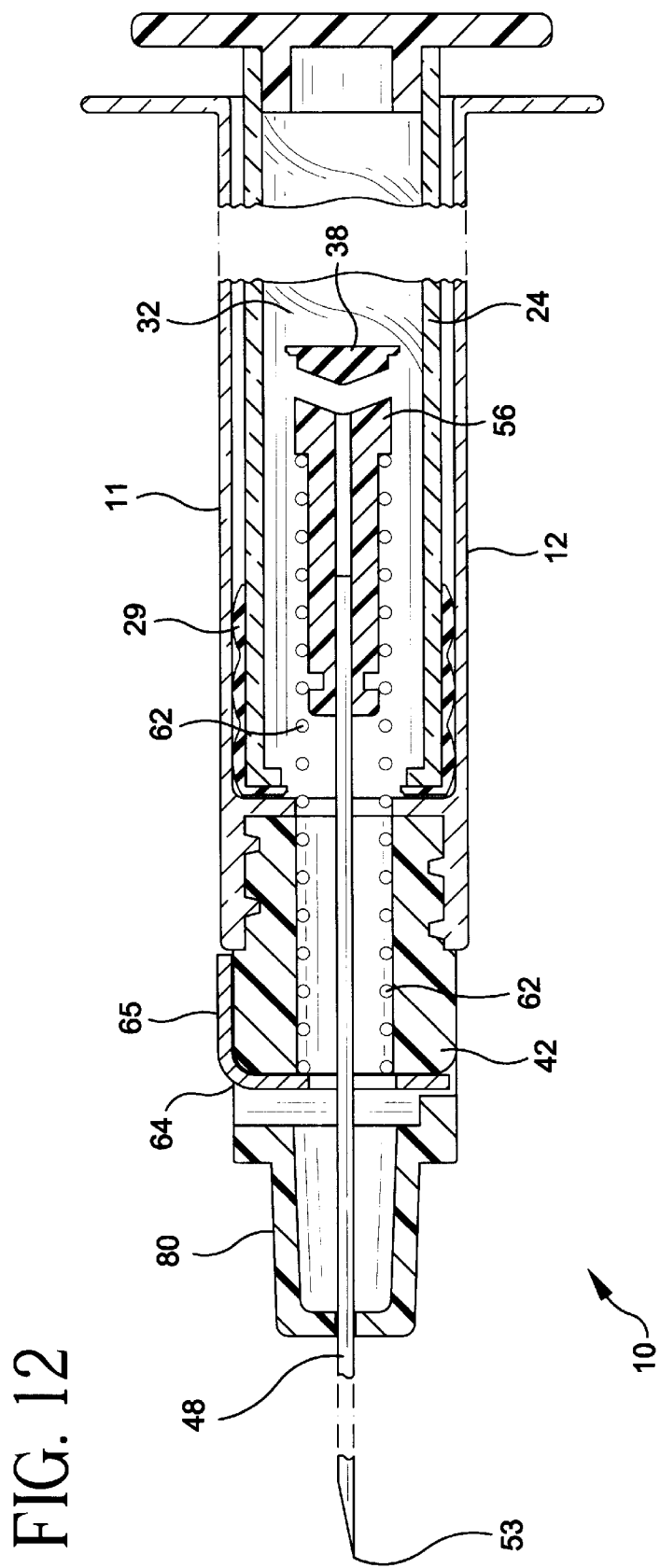
FIG. 12 is a schematic cross-sectional view of the embodiment of FIG. 11, with the latch in the release position and with the needle and the mount partially withdrawn into the cavity in the plunger.

Syringe assembly 10 also has a spring 62 disposed about mount 56 biased to urge slidable movement of needle 48 from the first position to the second position. Syringe 10 includes a selectively releasable latch 64, best seen in FIGS. 3, 4, and 5, disposed in hub 42 to engage mount 56 and retain the mount and needle 48 in the first position. Referring to FIG. 8, latch 64, for selectively releasing mount 56 and needle 42 to move from the first position to the second position, preferably includes an accessible release, such as a finger press area 65 so that the practitioner can selectively release latch 64 by application of a finger with sufficient force to finger press 65.

Figure 3:
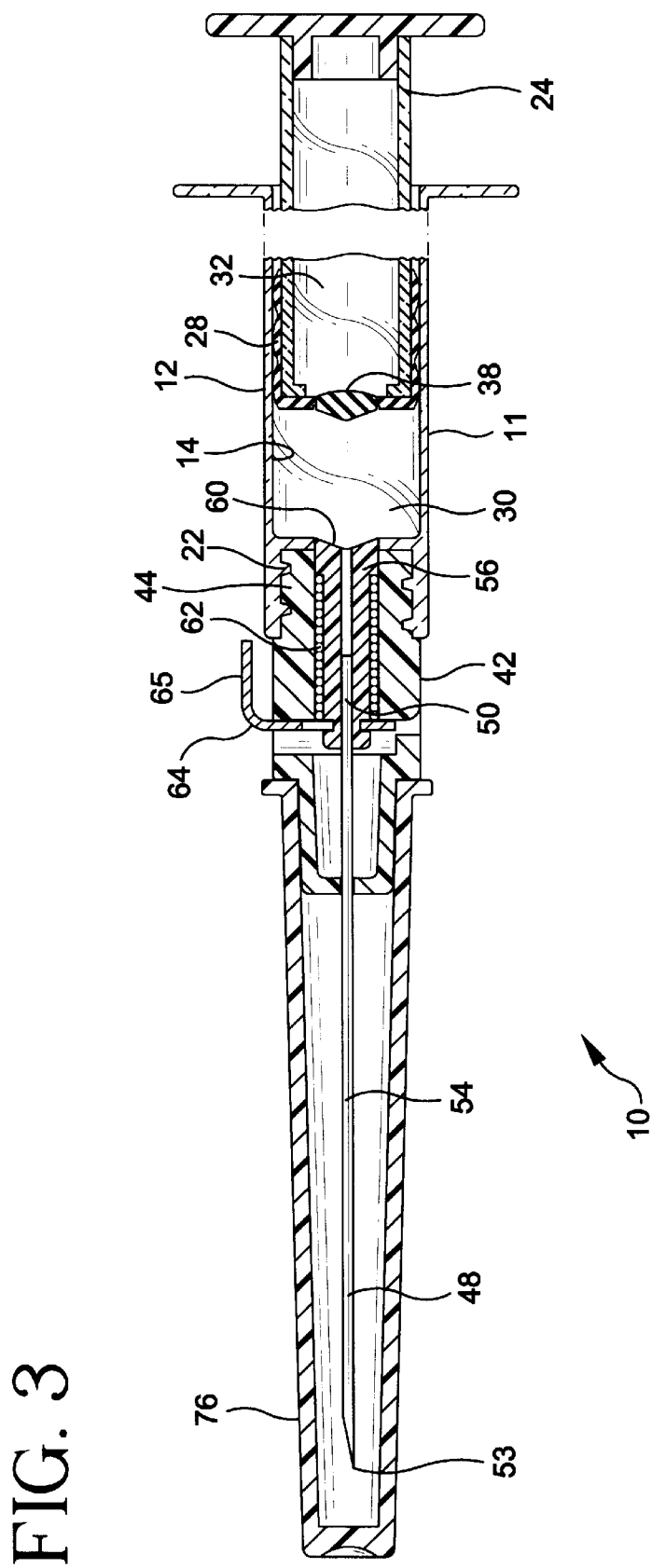
FIG. 3 is a schematic cross-sectional view, analogous to FIG. 2, of the syringe of the invention with the needle hub mounted on the syringe.
Figure 4:
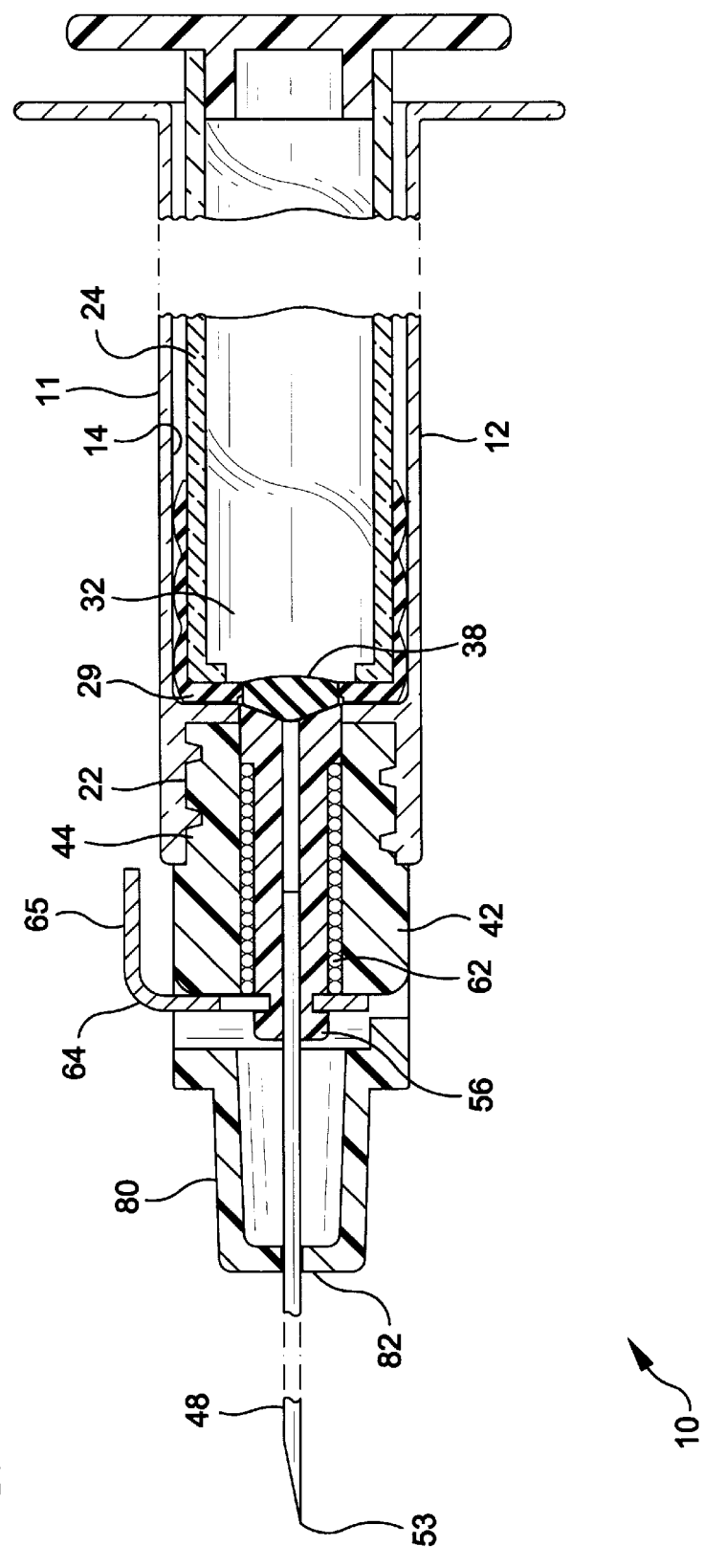
FIG. 4 is a schematic cross-sectional view, analogous to FIGS. 2 and 3, of the syringe of the invention with the needle exposed and the plunger depressed to expel the contents.

Referring to FIG. 8, latch 64 preferably has an opening 66 therethrough, that has a first portion 68 and a second portion 69, first portion 68 preferably being sized to engage mount 56 at an engagement 57 to retain mount 56 in hub 42 in the first position, best seen in FIGS. 3 and 4, when latch 64 is disposed in the latch position. Second portion 69 of opening 66 is sized to allow disengagement of mount 56 from latch 64 when the practitioner selectively releases the latch by the application of sufficient force to finger press area 65 to move the latch to the release position, thereby allowing spring 62 to urge movement of mount 56 and needle 48 from the first position, where needle 48 projects outwardly, to the second position, best seen in FIG. 6, where mount 56 and needle 48 are substantially within cavity 32 in the plunger thereby substantially protecting the medical practitioner and others from inadvertent contact with needle 48 once latch 64 is released. The movement of the mount and the needle into cavity 32 in the plunger also renders syringe assembly 10 and needle 48 substantially non-reusable.

Figure 5:
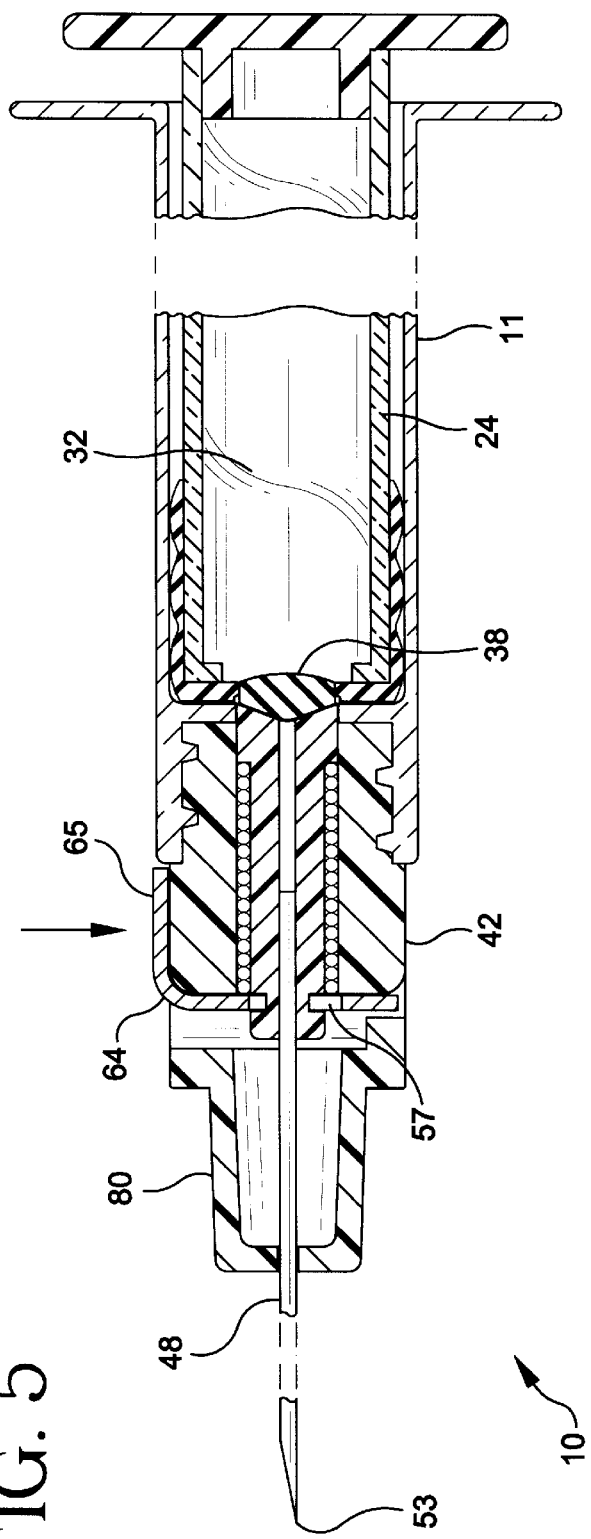
FIG. 5 is another schematic cross-sectional view, analogous to FIGS. 2, 3, and 4, of the syringe of the invention with the latch in the hub in the release position.
Figure 6:
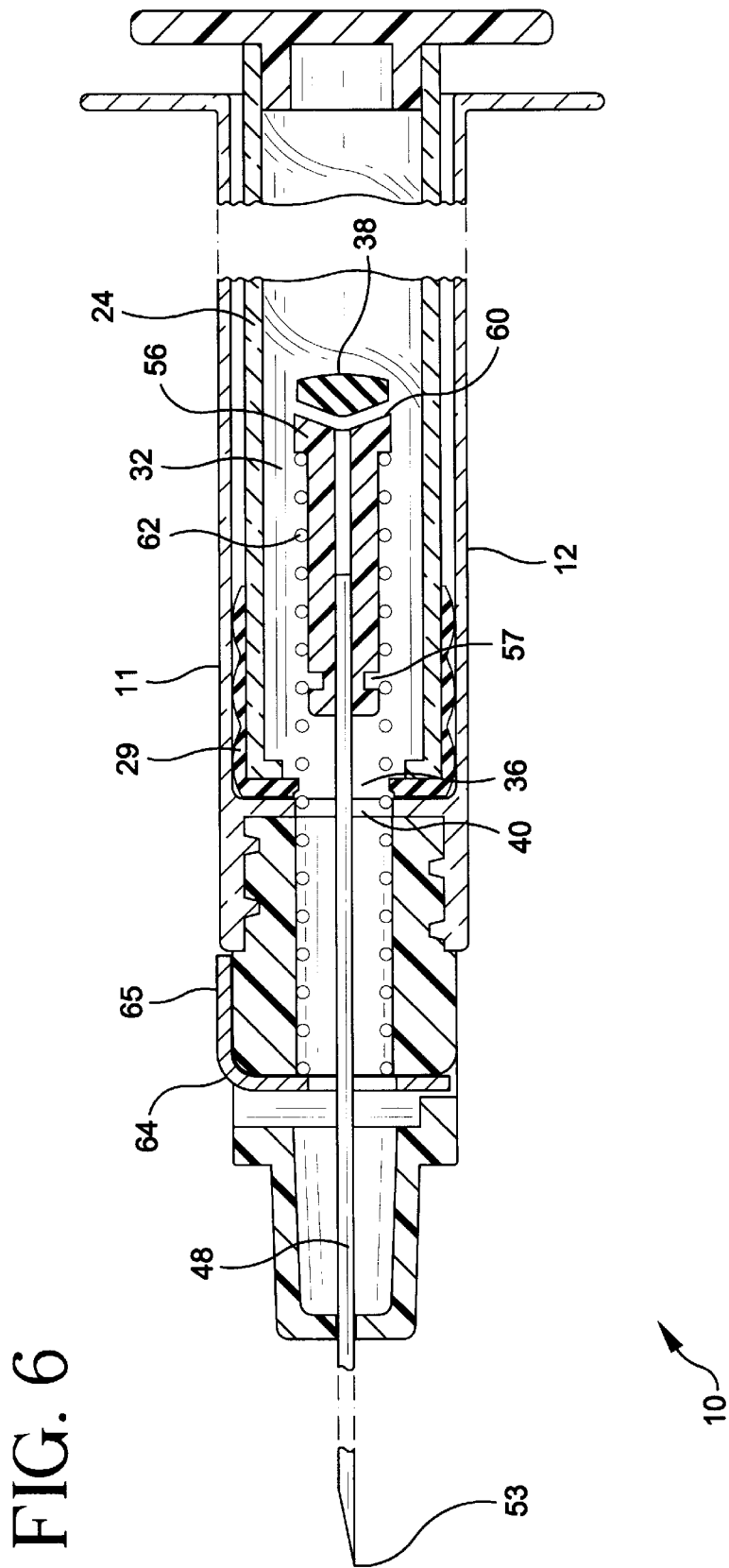
FIG. 6 is a further schematic cross-sectional view, analogous to FIG. 5, with the needle and mount partially retracted into the cavity in the plunger.
Figure 7:
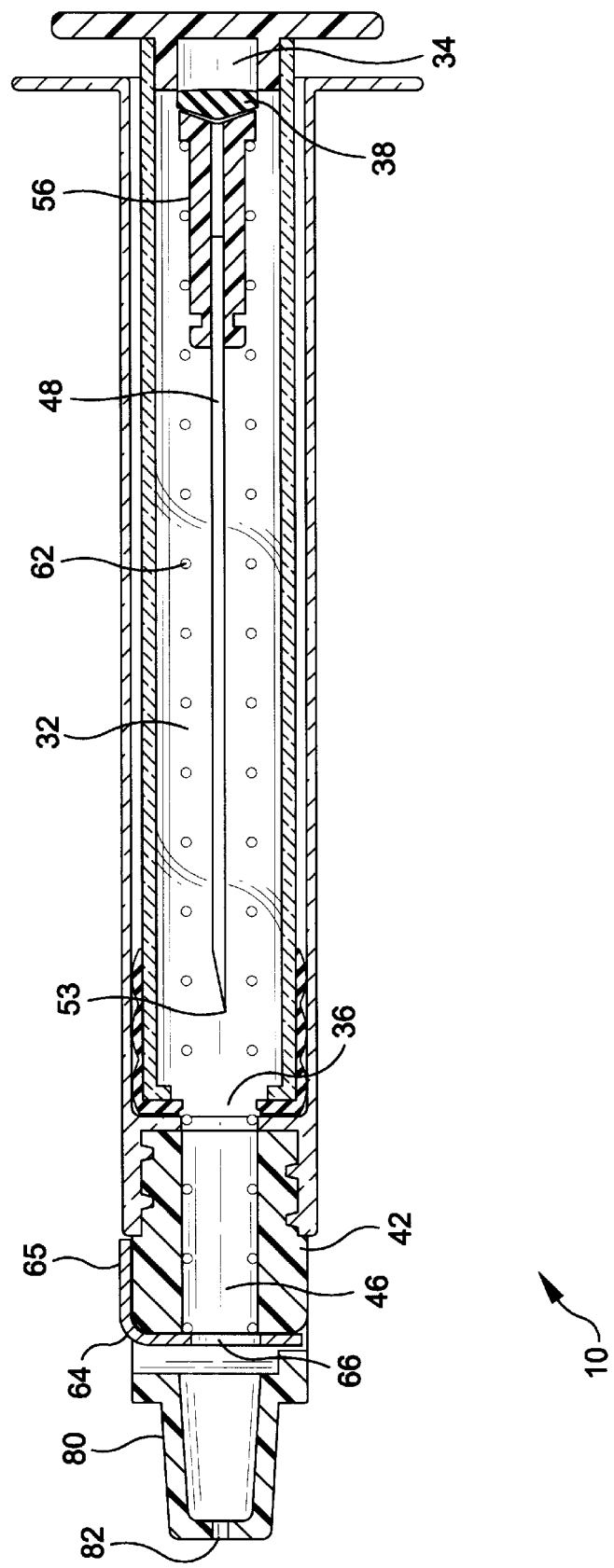
FIG. 7 is a schematic cross-sectional view, analogous to FIG. 6, with the needle, mount and spring substantially within the cavity in the plunger.

Referring to FIGS. 5, 6 and 7, the release of mount 56 from latch 64, the displacement of selectively releasable closure 38 and movement of mount 56 and needle 48 into cavity 32 is shown. In this preferred embodiment, selectively releasable closure 38 for closing cavity 32 in the plunger is a plug that is displaced from a position, best seen in FIGS. 5 and 6, where the distal end of cavity 32 is closed, to a position where the distal end of cavity 32 is open, by mount 56 when needle 48 and mount 56 move from the first position after the practitioner releases the selectively releasable latch.

Closure 38 serves an important purpose in syringe 11 of the invention. Earlier disclosures of a syringe with a retractable needle do not recognize the need for practitioners to be able to substantially expel the contents of chamber 30. In the present invention, chamber 30 within plunger 24 is isolated from the fluid path of the syringe by closure 38. Thus a practitioner is able to use syringe 10 for substantially any purpose that a syringe would normally be used for, then when the desired usage is completed, then the practitioner positions plunger 24 in the distal position within the barrel, selectively releases the latch to allow spring 62 to urge mount 56 and needle 48 proximally to displace closure 38 and to withdraw the needle into cavity 32.

Figure 5A:
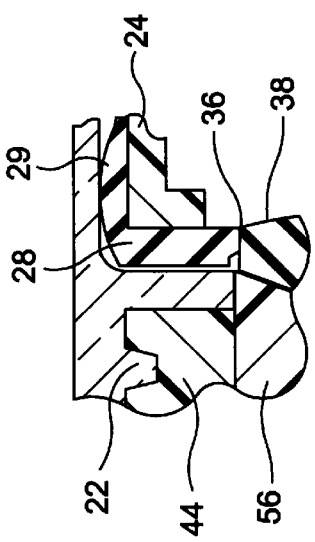
FIG. 5a is an enlarged schematic cross-section view of a portion of the view of FIG. 5.

Referring to FIGS. 5 and 5a, closure 38 has a point of attachment 39 distal end 28 of plunger 24. In a preferred embodiment, distal end 28 of the plunger includes a formed resilient stopper 29 that forms the liquid tight seal with the inside surface of the barrel, with closure 38 being held by an interference fit, friction fit, snap-fit or the like into plunger 24. Referring to FIG. 5a, point of attachment 39 is sufficiently releasably that, when plunger 24 is distal in barrel 12, and latch 64 is released by the practitioner, spring 62 urges mount 56 to allow closure 38 to be displaced by mount 56 causing point of attachment 39 to disengage from plunger 29, thereby clearing cavity 32 to accept mount 56 and needle 48. As shown in FIGS. 5 and 5a, point of attachment 39 releases to allow closure 38 to be displaced.

In a more preferred embodiment, best seen in FIGS. 9–12, mount 56 proximal end 58 preferably projects proximally into chamber 30. In this embodiment, when plunger 24 is fully depressed distally into syringe barrel 12, substantially all of the contents of the chamber are displaced, providing substantially no "dead-space". When the practitioner has completed the used of the syringe, additional distal pressure applied to plunger 24 distorts plug 38 and frangibly disrupts point of attachment 39 so that when latch 64 is released by the practitioner, plug 38 is displaced and so that mount 56 and needle 48 are urged into cavity 32 by spring 62. In this embodiment, plug 38 is preferably integrally formed with stopper 24 with attachment point 39 being formed as an area of reduced thickness or a weakened area that may be readily frangibly disrupted when the practitioner applies sufficient distal pressure.

Preferably, syringe assembly 10 further includes a removable shield 76 over needle 48 to protect the needle from inadvertent exposure. Distal end 52 of needle 48 preferably is formed into a sharpened point 53 to facilitate hypodermic penetration.

Hub 42 preferably includes a needle guide portion 80 disposed distally on said hub having an axial opening 82 therethrough. Opening 82 is sized and positioned to maintain needle 48 substantially axially aligned with barrel 12 when mount 56 and needle 48 are in the first position and to allow the proximal withdrawal of needle 48 when latch 64 is released.

Referring to the Figs., fitting 22 on the distal end of syringe 11 is conjugate to fitting 44 on hub 42. As shown in the Figs., hub 42 is releasably assembled to syringe 11 to form syringe assembly 10. Fittings 22 and 44 may be threads, snap-fit, press-fit or any other type of releasable attachment. A constraint on the fittings 22 and 44 is that conjugate luer fittings would not be suitable for most applications of the invention, since most male luer fittings would not allow sufficient clearance for the slidable movement through the fitting of mount 56 with needle 48 into cavity 32. Additionally, conventional luer syringes do not have a cavity 32 in their plunger to receive the mount and needle when latch 64 is released by the practitioner, thus if fitting 44 were a luer type fitting and hub 42 was mounted on a luer fitting the needle assembly of the invention could not function as intended. For particular applications, it may be desirable to supply hub 42 with a variety of needle sizes to be affixed to syringe 11 by the practitioner. Alternatively, assembly 10 could be supplied with hub 42 fixedly attached to syringe 11, either by integrally forming hub 42 with barrel 12 or with a suitable attachment, including spin-weld, adhesive bonding, laser weld, thermal bonding, heat staking, solvent bonding or other fixed attachments that provide sufficient rigidity for assembly 10 to function properly.

Figure 2:
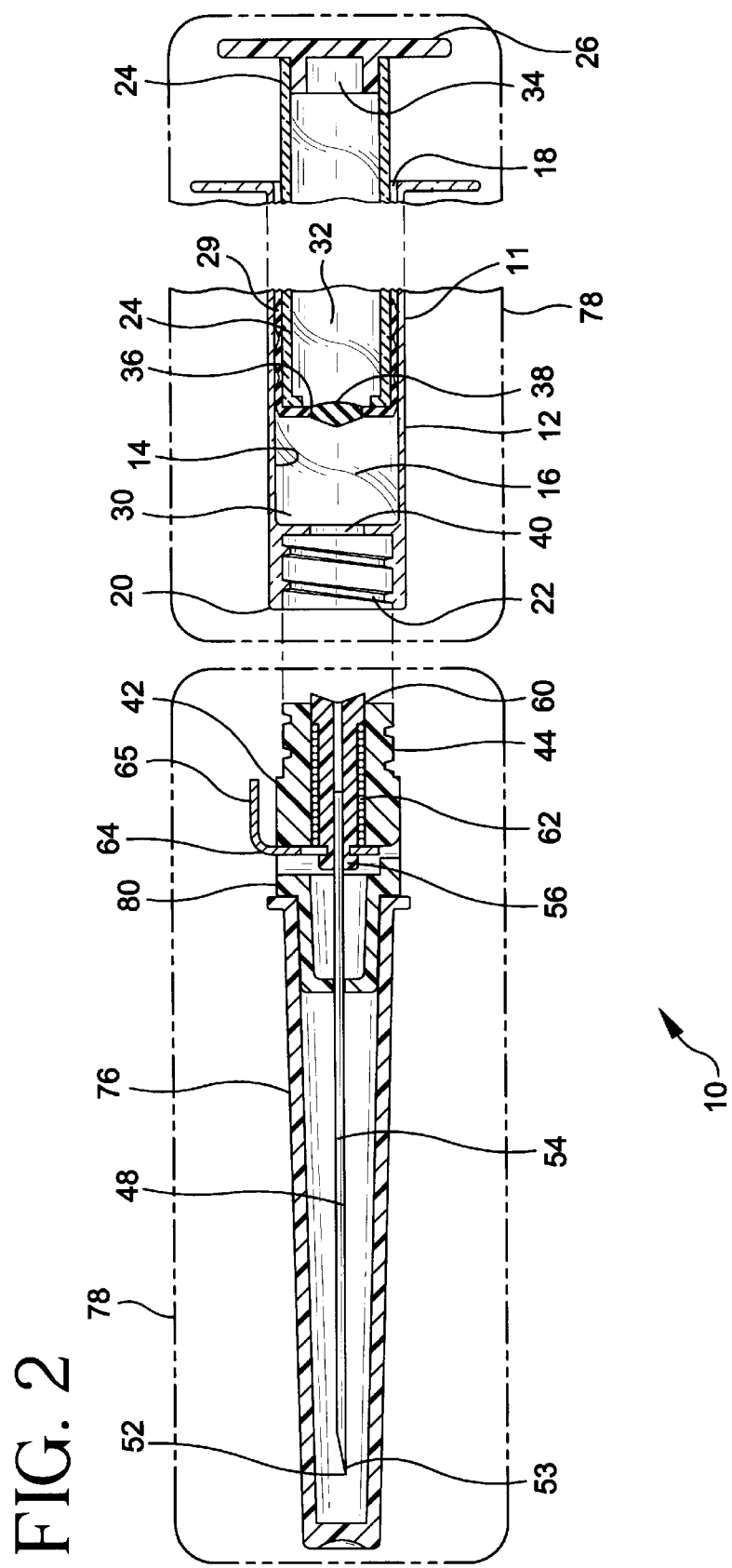
FIG. 2 is a schematic cross-sectional view of the syringe and needle of FIG. 1, taken along the line 2—2.

As shown in phantom in FIGS. 1 and 2, syringe assembly 10 is preferably placed in a package 78 formed from materials substantially resistant to the passage of microorganisms and exposed to conditions that render any microorganisms inside package 78 substantially non-viable. Package 78 may be formed from materials such as paper, non-wovens, polymeric films and combinations of these materials. Conditions for rendering microorganisms substantially non-viable include, but are not limited to, exposure to ionizing radiation, and chemical agents such as ethylene oxide and vapor phase hydrogen peroxide. After a sufficient exposure, syringe assembly 10 may be considered sterile until package 78 is opened prior to use. In selecting materials for package 78 and for forming syringe assembly 10, consideration of the compatibility of the materials with the planned sterilization method is made. As shown in FIG. 2, an needle assembly including shield 76, needle 48, hub 42 and mount 56 may be packaged in packages 78 separately from syringe 11 so that a range of sizes of needle 48 may be offered to practitioners.

Suitable materials for forming plunger 24, shield 76 and barrel 12 of syringe 11 include but are not limited to polypropylene, polycarbonate, polystyrene and the like. Plug 38 may be formed from resilient thermoset or thermoplastic elastomers. Mount 56 and hub 42 may be formed from polypropylene, polycarbonate, polystyrene and the like. Latch 64 may be formed from a metallic material such as a stainless steel or a rigid thermoplastic. Spring 62 is preferably formed from a metallic material such as a suitable stainless steel.

Figure 13:
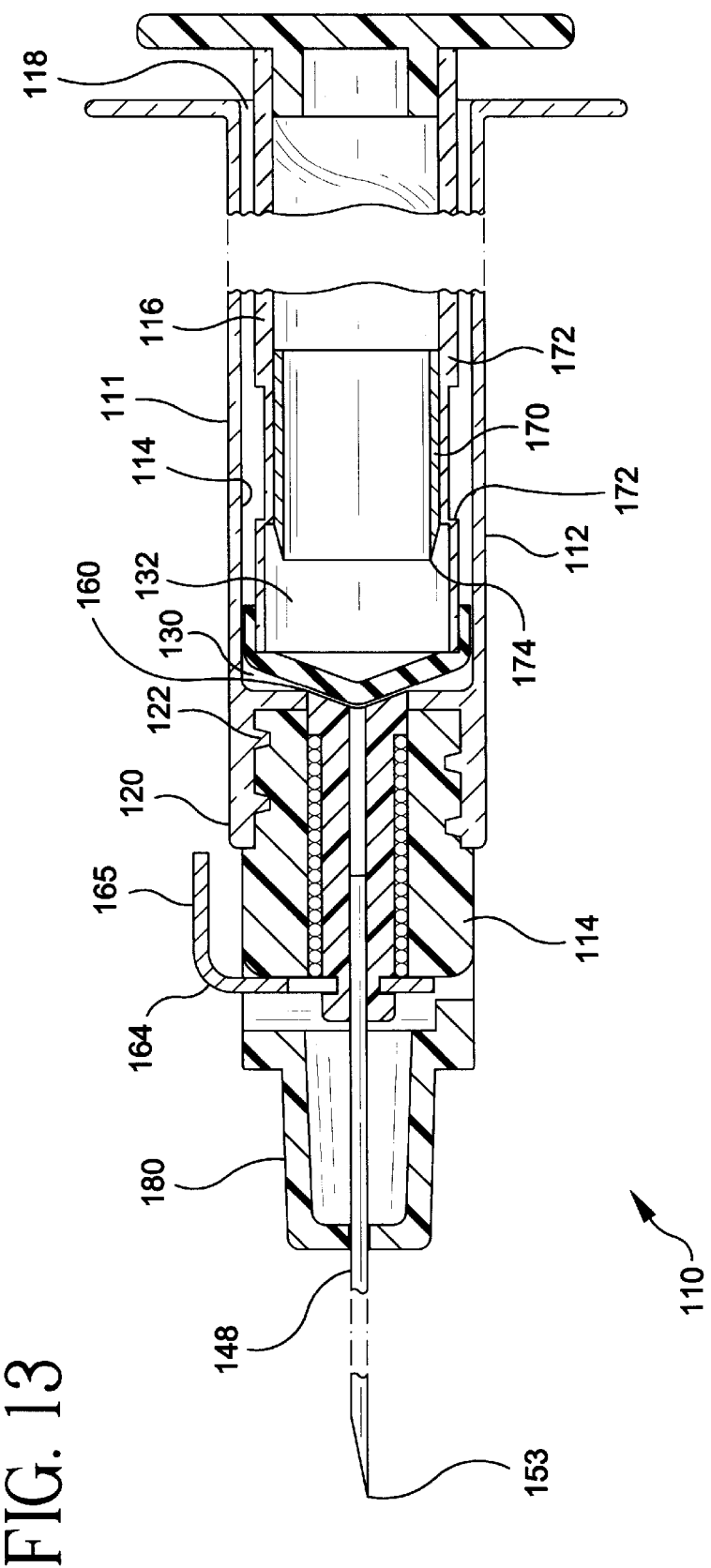
FIG. 13 is a schematic cross-sectional view of another embodiment of the syringe of FIG. 1, analogous to the view of FIG. 4, with the plunger depressed sufficiently to expel the contents of the syringe.
Figure 14:
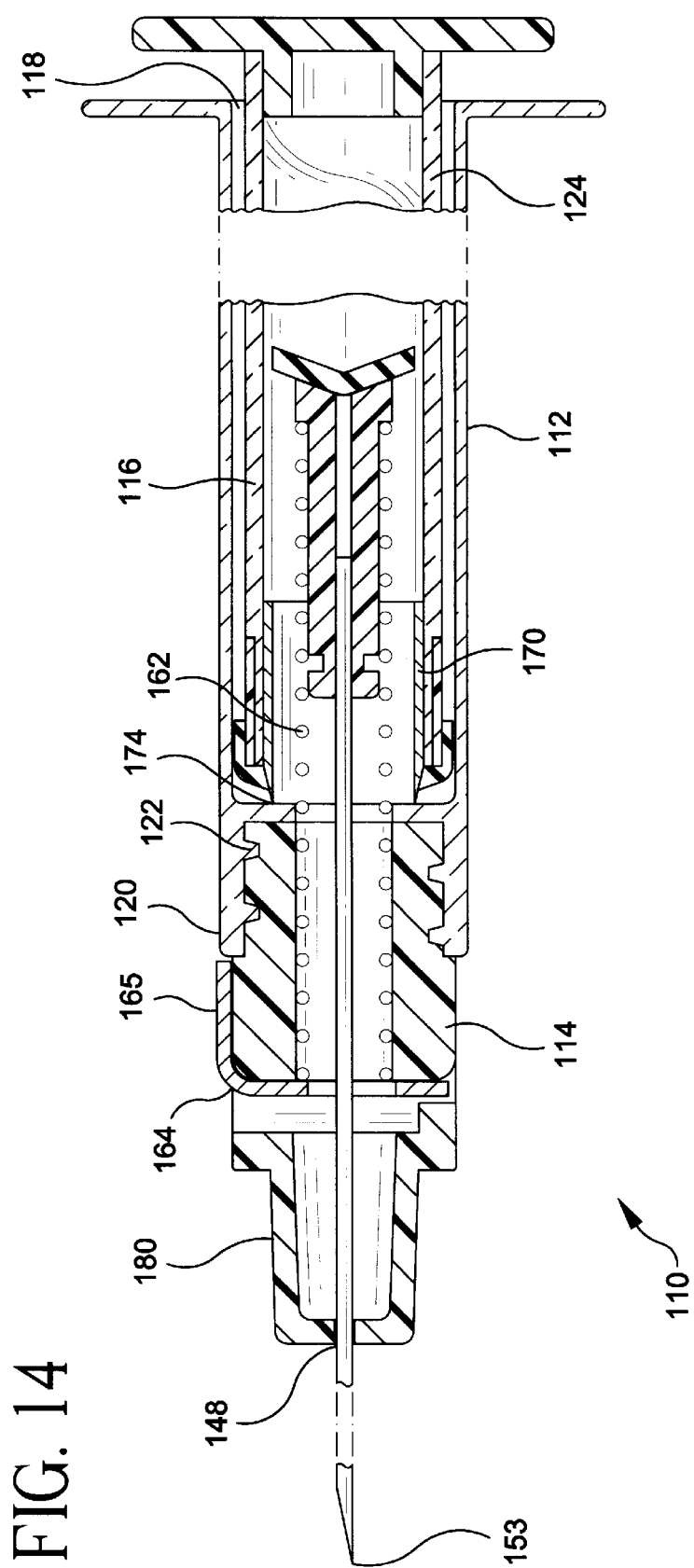
FIG. 14 is a schematic cross-sectional view of the embodiment of FIG. 13, showing the effect of depressing the plunger beyond the amount necessary to expel the contents of the syringe, the latch in the release position, and with the needle and the mount partially withdrawn into the cavity in the plunger.

Referring now to FIGS. 13 and 14, an additional embodiment of syringe assembly 10 is shown. In this embodiment, substantially similar elements, performing substantially similar functions are identified with reference characters similar to those of FIGS. 1–12, with the addition of hundreds digits. Referring to FIGS. 13–14, a hypodermic syringe assembly 110 of the invention that is useful for drawing, containing and delivering liquids includes a syringe 111 with an elongate barrel 112 defining an axis, an inside surface 114, an open bore 116 therethrough having an open proximal end 118 and a distal end 120 that includes a fitting 122. Syringe assembly 110 also has an elongate plunger 124 having a proximal end 126 and a distal end 128, plunger 124 is sized for slidable movement within open bore 116 of barrel 112 thereby defining a chamber 130 proximal to distal end 120 of the barrel within barrel 112. Chamber 130 allows for drawing, containing and delivering liquids, with distal end 128 of plunger 124 forming a substantially liquid tight seal with inside surface 114 of barrel 112. Plunger 124 also has an elongate cavity 132 therewithin, best seen in FIG. 13, that has a closed proximal end 134 and an open distal end 136. Open distal end 136 of plunger 124 is closed by a selectively releasable closure 138 integrally formed as a plunger stopper 139. Plunger 124 includes a cutting member 170 disposed within cavity 132. Plunger 124 includes a formed weakened portion 172, preferably of thin cross-section, that is frangibly collapsible by a practitioner's application of a sufficient distal pressure on the plunger to allow the plunger to partially axially collapse. This partial axial collapse of the plunger causes a cutting surface 174 of cutting member 170 to engage plunger stopper 139 and cut an opening therethrough to into chamber 130. When the practitioner releases latch 164, spring 162 proximally urges mount 156 with needle 148 into cavity 132 as shown in FIG. 14.

Additionally, fitting 122 at distal end 120 of barrel 112 has a passageway 140 therethrough into chamber 130 of the barrel 112. Syringe 110 of the invention has a hub 142 that attaches to 112 barrel with a fitting 144 conjugate to fitting 122 at distal end 120 of the barrel 112, hub 142 having a passageway 146 therethrough communicative to chamber 130 in barrel 112 when hub 142 is attached to barrel 112. Hub 142 further includes an elongate needle 148 having a proximal end 150, a distal end 152 and a fluid path 154 therethrough. Needle 148 is positioned through in passageway 140 for slidable movement between a first position, best seen in FIG. 13, wherein fluid path 154 of needle 148 is in fluid communication with chamber 130 in the barrel and distal end 152 of the needle projecting outwardly from hub 142 and a second position. Needle 142 has a mount 156 at proximal end 150 with a mount proximal end 158 of the mount having a seal portion 160 for forming a seal with chamber 130 at the distal end of the barrel when needle 148 is in the first position so that a movement of plunger 124 within the barrel can draw into and expel a liquid from chamber 130 through fluid path 154 of needle 148.

Syringe 110 also has a spring 162 disposed about mount 156 biased to urge slidable movement of needle 148 from the first position to the second position. Syringe 110 includes a selectively releasable latch 164, disposed in hub 142 to engage mount 156 and retain the mount and needle 148 in the first position.

Figure 15:
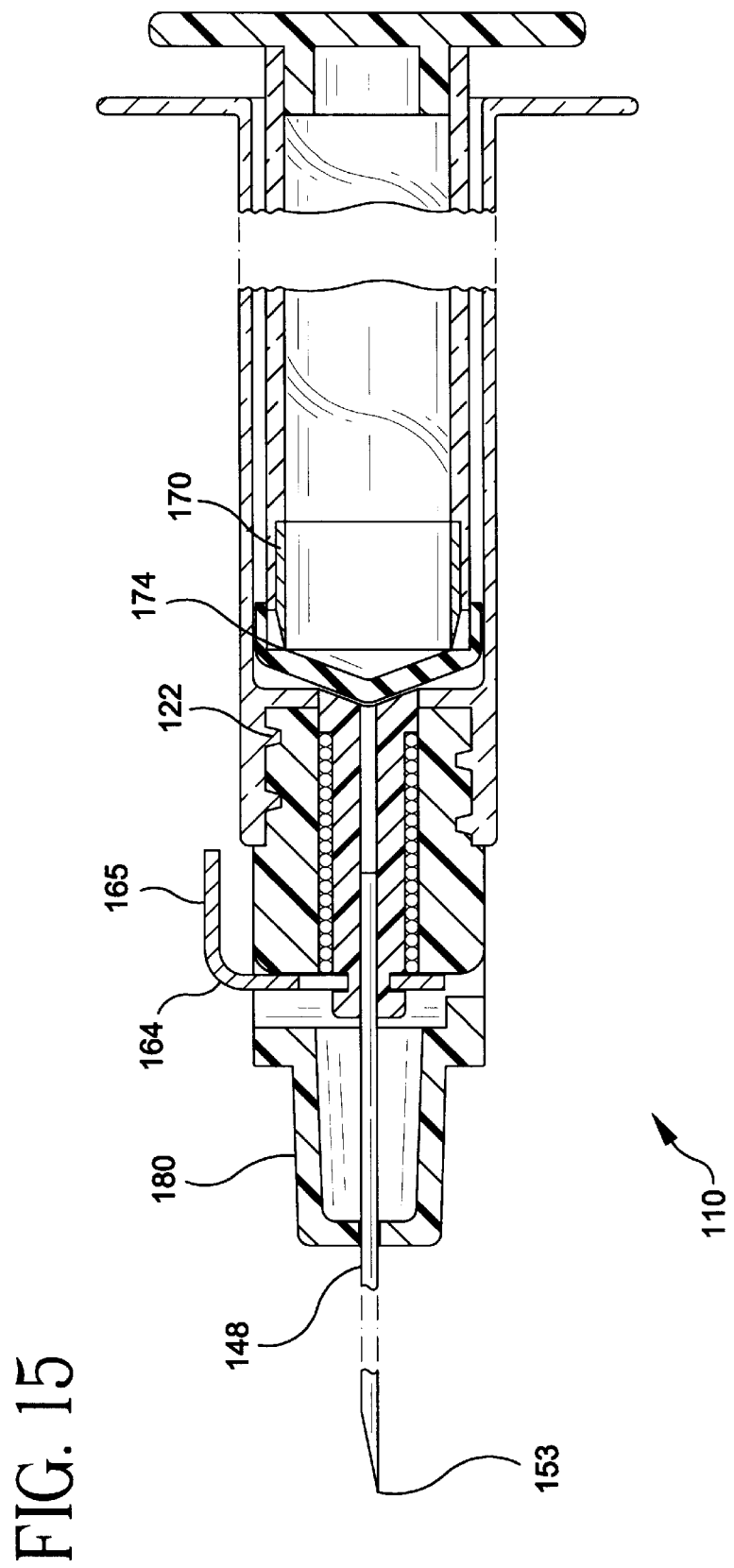
FIG. 15 is a schematic cross-sectional view of a further embodiment of FIG. 13, with the plunger depressed sufficiently to expel the contents of the syringe.
Figure 16:
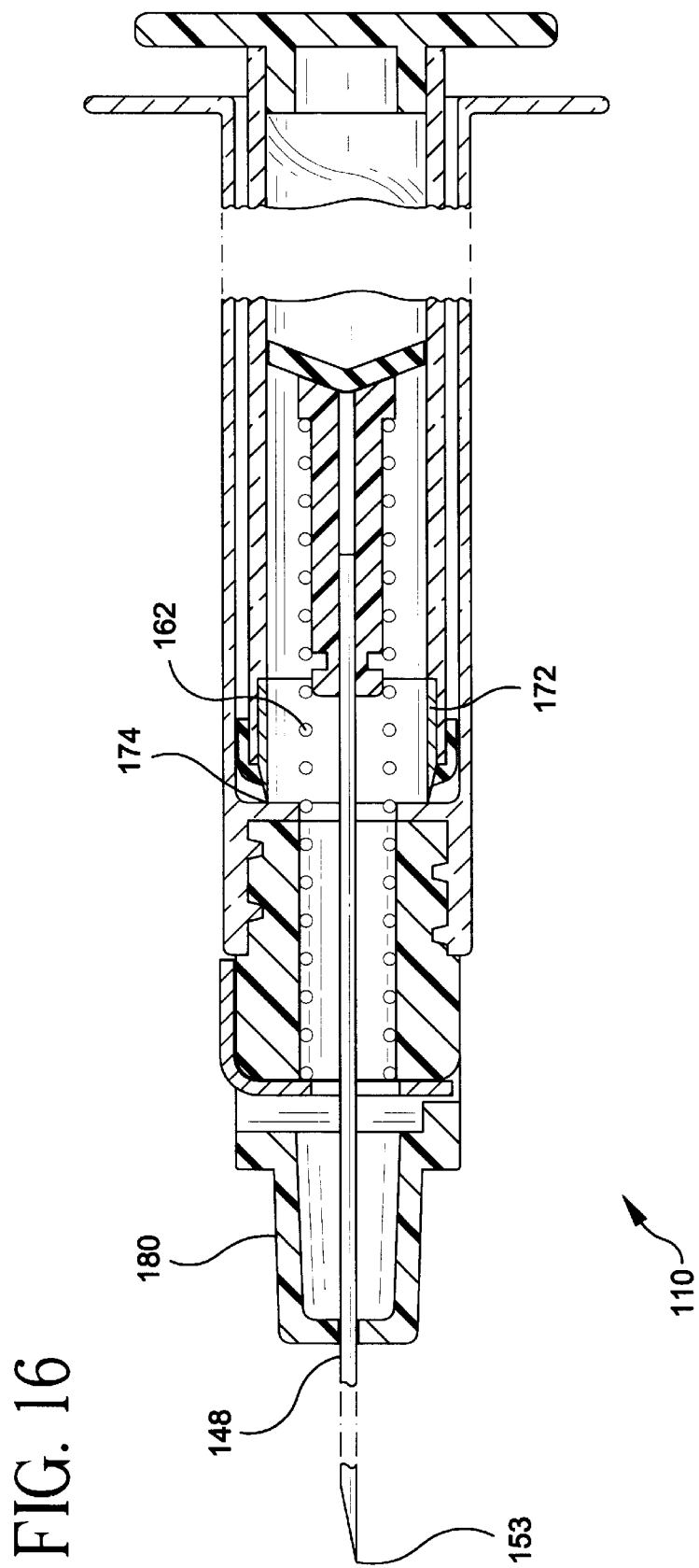
FIG. 16 is a schematic cross-sectional view of the embodiment of FIG. 15, showing the effect of depressing the plunger beyond the amount necessary to expel the contents of the syringe, the latch in the release position and with the needle and the mount partially withdrawn into the cavity in the plunger.

A variation on the embodiment shown in FIGS. 13 and 14 is shown in FIGS. 15 and 16. In this embodiment, cutter 170 is disposed substantially adjacent to stopper 139, so that as the practitioner applies a distal force to plunger 124 beyond that required to displace any fluid from chamber 130, cutter 170 engages stopper 139 and cuts through it to provide an opening into cavity 132 so that when the practitioner releases latch 164, spring 162 urges mount 156 and needle 142 into cavity 132 displacing cut portion 138 of stopper 139 that had functioned as the closure for the cavity.

The hypodermic syringe assembly of the invention provides practitioners with a selectively releasable retractable needle that is substantially usable as a conventional syringe in most procedures. The contents of the syringe of the invention may be drawn and expelled by the practitioner in a similar fashion to a conventional syringe, without concern regarding retention of the contents in excessive "dead-space". The particular benefit of the syringe of the invention is its conventional utility coupled to the practitioner selected ability to readily render the syringe sharp portion substantially free from inadvertent or misdirected reuse by simply bottoming the plunger in the barrel and releasing the latch to allow the spring to urge the hub and needle into the cavity in the plunger.

What is claimed is:

1. A hypodermic syringe assembly useful for drawing, containing and delivering liquids comprising:

a syringe with an elongate barrel defining an axis, said barrel having an inside surface, an open bore therethrough having an open proximal end and a distal end comprising a fitting;

an elongate plunger having a proximal end and a distal end, said plunger being disposed within said barrel and sized for slidable movement within said open bore of said barrel thereby defining a chamber proximal to said distal end of said barrel within said barrel for drawing, containing and delivering liquids, said distal end of said plunger forming a substantially liquid tight seal with said inside surface of said barrel, said plunger having an elongate cavity therewithin having a closed proximal end and an open distal end; said open distal end of said plunger being closed by a selectively releasable closure and wherein said fitting at said distal end of said barrel has a passageway therethrough into said chamber of said barrel;

a hub having a fitting conjugate to said fitting at said distal end of said barrel for attaching said hub to said barrel, said hub having a passageway therethrough communicative to said chamber in said barrel when said hub is attached to said barrel, said hub further including an elongate needle having a proximal end, a distal end and a fluid path therethrough, said needle being disposed through said passageway for slidable movement between a first position wherein said fluid path of said needle is in fluid communication with said chamber in said barrel and said distal end of said needle projects outwardly from said hub and a second position, said needle having a mount at said proximal end, said mount having a proximal end having a seal portion for forming a seal with said chamber at said distal end of said barrel when said needle is in said first position so that a movement of said plunger within said barrel can draw into and expel a liquid from said chamber through said fluid path of said needle;

a spring disposed about said mount being biased to urge said slidable movement of said needle from said first position to said second position;

a selectively releasable latch disposed in said hub to engage said mount and retain said mount and said needle in said first position, said latch being selectively releasable by a practitioner so that said spring urges said mount and said needle to move from said first position into said second position, said second position being substantially within said cavity in said plunger, thereby substantially protecting the medical practitioner from inadvertent contact with said needle once said latch is released and rendering said syringe and needle substantially non-reusable.

2. The syringe of claim 1 wherein said selectively releasable closure for closing said cavity in said plunger further comprises a plug, said plug being displaced from a position wherein said distal end of said cavity is closed to a position wherein said distal end of said cavity is open, by said mount when said needle and said mount move from said first position to said second position after the practitioner releases said selectively releasable latch.

3. The syringe assembly of claim 2 wherein said selectively releasable closure for closing said cavity further comprises said seal portion of said mount being sized to extend a sufficient distance proximally into said chamber so that when said plunger is depressed distally against said seal portion with a force greater than a force required to expel substantially all liquid in said chamber, said plug thereby being displaced from closing said cavity allowing said mount and said needle to move into said second position when the practitioner releases said latch.

4. The syringe assembly of claim 3 wherein said selectively releasable closure for closing said cavity further comprises one of said plug and said distal end of said plunger including a frangible portion so that when said plunger is depressed against said seal portion with the force greater than the force required to expel substantially all liquid in said cavity, said frangible portion is ruptured with said distal end of said cavity being opened, thereby allowing said mount and said needle to move from said first position to said second position into said cavity when said latch is released by the practitioner.

5. The syringe assembly of claim 1 wherein said latch for selectively releasing said mount and said needle to move from said first position to said second position further comprises release means so that the practitioner can selectively release said latch by application of a sufficient force to said release means.

6. The syringe assembly of claim 1 wherein said release means for said latch further comprises said latch having a finger press area accessible to the practitioner's finger, thereby allowing the selective release of said latch by application of sufficient force by the practitioner's finger.

7. The syringe assembly of claim 6 further comprising said latch having an opening therethrough, said opening having a first portion and a second portion, said first portion being sized to engage said mount at an engagement to retain said mount in said hub in said first position when said latch is disposed in said latch position, said second portion of said opening being sized to allow disengagement of said mount from said latch when the practitioner selectively releases said latch by application of a sufficient force to said finger press area to move said latch to the release position, thereby allowing said spring to urge movement of said mount and said needle from the first position, where said needle projects outwardly, to said second position, where said mount and said needle are substantially within said cavity in said plunger thereby substantially protecting the practitioner from inadvertent contact with said needle.

8. The syringe assembly of claim 1 wherein said selectively releasable closure for said cavity in said plunger further comprises a cutting member having a cutting surface being disposed proximal to said distal end of said plunger within said cavity so that when said plunger is depressed distally with a sufficient force, said closure is deflected onto said cutting surface of said cutting member so that a sufficient portion of said closure is cut through to expose said cavity in said plunger for receipt of said mount and said needle when the practitioner selectively releases said latch to allow said spring to urge said movement of said mount and said needle from said first position to said second position.

9. The syringe assembly of claim 7 wherein said plunger having said cutting member further comprises said plunger being axially collapsible by having an area of reduced thickness comprising a weakened area so that when said plunger is depressed distally with a sufficient force, said area of reduced thickness is frangibly detached, thereby allowing said depressing force to urge said cutter having said cutting surface to engage said closure and cut through a sufficient portion of said closure to expose said cavity in said plunger for receipt of said mount and said needle when the practitioner selectively releases said latch.

10. The syringe assembly of claim 7 wherein said cover of said cavity and said seal at said distal end of said plunger further comprise said cover and said seal being formed from a single material as a single article of manufacture having a unitary structure.

11. The syringe assembly of claim 1 further comprising a removable shield over said needle.

12. The syringe assembly of claim 1 wherein said fitting at said distal end of said syringe barrel and said conjugate fitting on said hub are conjugate fittings, not including luer fittings, so that said hub having said mount and said needle is selectively attachable and detachable from said barrel.

13. The syringe assembly of claim 1 being sealed in a package formed from materials substantially resistant to the passage of microorganisms and being exposed to conditions sufficient to render any microorganisms therein substantially non-viable.

14. The syringe assembly of claim 1 wherein said needle assembly including said hub, said needle, said mount and said shield being sealed in a package separate from said syringe and exposed to conditions sufficient to render any microorganisms therein substantially non-viable, said package being formed from materials substantially resistant to microorganisms, thereby substantially protecting said hub with said needle from microbial contamination until said package is opened.

15. The syringe assembly of claim 12 wherein said materials for forming said package are selected from the group consisting of paper, polymeric film, non-wovens, metal foils and combinations thereof.

16. The syringe assembly of claim 1 wherein said fitting at said distal end of said barrel and said conjugate fitting on said hub are not disengageable once engaged, thereby forming a fixed attachment of said hub to said barrel.

17. The syringe assembly of claim 16 wherein said fixed attachment of said hub to said barrel further comprises an application of a bonding selected from the group spin-welding, sonic-welding, heat-stake, laser-weld, thermal-bonding, mechanical snap-fit, press-fit, adhesive, solvent and combinations thereof.

18. The syringe assembly of claim 16 wherein said fixed attachment of said hub to said barrel further comprises said hub being integrally formed as a part of said barrel.

19. The syringe assembly of claim 1 wherein said distal end of said needle comprises a sharpened point to facilitate a penetration of said needle.

20. The syringe assembly of claim 1 wherein said hub further comprises a needle guide portion disposed distally on said hub having an axial opening therethrough, said opening being sized and positioned to maintain said needle substantially axially aligned with said barrel when said mount and said needle are in said first position.

* * * * *